United States Patent
Piveteau et al.

(10) Patent No.: US 6,221,111 B1
(45) Date of Patent: Apr. 24, 2001

(54) BIOACTIVE SURFACE LAYER FOR BONE IMPLANTS

(75) Inventors: Laurent Dominique Piveteau, Fribourg; Beat Gasser, Ittigen; Louis Schlapbach, Muri, all of (CH)

(73) Assignee: Dr. H. C. Robert Mathys Stiftung, Bettlach (CH)

( * ) Notice: Subject to any disclaimer, the term of this patent is extended or adjusted under 35 U.S.C. 154(b) by 0 days.

(21) Appl. No.: 09/331,698

(22) PCT Filed: Dec. 23, 1996

(86) PCT No.: PCT/CH96/00461

§ 371 Date: Jun. 23, 1999

§ 102(e) Date: Jun. 23, 1999

(87) PCT Pub. No.: WO98/28025

PCT Pub. Date: Jul. 2, 1998

(51) Int. Cl.[7] .......................................................... A61F 2/02
(52) U.S. Cl. ............................................................. 623/23.57
(58) Field of Search ............................... 623/16.11, 20.17, 623/23.28, 23.29, 23.3, 23.36, 23.51, 23.56, 23.57, 23.6, 23.61, 23.75, 23.76

(56) References Cited

FOREIGN PATENT DOCUMENTS

| 34 12 915 | 10/1984 | (DE) . |
| 211 676 | 2/1987 | (EP) . |
| 232 791 | 8/1987 | (EP) . |
| 264 917 | 4/1988 | (EP) . |
| WO 94/25637 | 11/1994 | (WO) . |
| WO 24391 | 8/1996 | (WO) . |

*Primary Examiner*—David J. Isabella
(74) *Attorney, Agent, or Firm*—Rankin, Hill, Porter & Clark LLP

(57) ABSTRACT

A bioactive surface layer with 0.01 $\mu$m to 5 mm thickness is suitable for a metallic bone implant. The surface layer has the following composition: (A) calcium compounds (CaX) consisting of crystalline calcium phosphate (CaP), calcium apatites (CaAp) and/or calcium carbonate ($CaCO_3$), in a proportion expressed by the following equation: 100% (CaX)=$\Sigma$[x % (CaP)+y % ($CaCO_3$)], in which x+y+z=100, $0 \leq x \leq 100$; $0 \leq y \leq 100$; $0 \leq z \leq 100$, and in the form of particles 20 nm to 4 mm; and (B) amorphous or crystalline metal oxide (MeO). The ratio between CAX and MeO in the surface layer can be preferably varied as a result of the specific coating process. The thickness of the surface layer lies between 0.01 $\mu$m and 5 mm and the CaX particles are 20 nm to 4 mm large.

28 Claims, No Drawings

BIOACTIVE SURFACE LAYER FOR BONE IMPLANTS

The invention relates to a surface layer for metal bone implants as defined in the preamble of claim 1. Metal bone implants and in particular those used as permanent implants are frequently coated with a bioactive layer to achieve permanent and stable anchoring in or on the bone. Alloplastic materials are considered bioactive if they chemically combine in firmly adhering manner to the vital bone tissue. Presently known surface layers are produced predominantly by plasma coating and incur various drawbacks; these include low adhesion to the substrate, unreliability in composition (crystal phase), no or few ways to vary the construction and composition of the layer, and especially the high cost of methods and production equipment.

Mixtures of metal oxide (MeO) and calcium phosphate (CaP) are already known in the state of the art, though specific medical applications have not yet been disclosed for them. In particular concrete data are lacking concerning the manufacture of such mixtures and their application as surface layers for surgical implants.

The objective of the invention is remedy. It aims to create a bioactive surface for bone implants on a metal substrate in such manner as to preclude separation between layer and substrate.

This problem is solved by the invention by a surface layer with the features of claim 1.

The surface layers of the invention are to be produced from mixtures of metal oxides and calcium compounds. Appropriate materials for coating bone implants on metal substrates are substances known as being bioactive or bio-inert. The substances denoted in the description below as metal oxides and calcium compounds are meant generically. Illustratively the bioactive surface layer may consist of titanium oxide and calcium hydroxyl apatite. The surface layers of the invention are free of layer/substrate separation between the metallic (substrate) phase and the ceramic phase (layer of oxide+calcium compound), and as a result abrasion or spalling of this ceramic surface layer in the event of non-uniform loading are precluded. The invention is especially significant for screw-shaped implants, whether for temporary implants (for instance Schanz screws) or for permanent anchoring (for instance oral implants). Furthermore these layers also may be impermeable or porous.

The anchoring of the implant fitted with a surface layer of the invention depending on configuration not only is locking in geometric manner but also is predominantly frictionally locking. This feature is caused by the chemical bonding between the bioactive surface layer and the abutting bone tissue resulting from the phase of one or more calcium compounds integrated into the surface layer.

Such surface layers may be prepared by wet-chemical procedures (for instance sol/gel technique; precipitation), thereby assuring good reproducibility and defined quality parameters. Moreover such procedures are comparatively simple and economical over the heretofore known methods (CVD, PVD or plasma spraying).

A preferred further development in making the surface layers of the invention allows different ways of constructing the layer. These osteo-conductive and bioactive surface layers may be impermeable or may be matched to a specific application using a freely selected porosity. Moreover the composition, for instance the MeO/CaP ratio, may be arbitrarily changed over the entire layer thickness to secure optimal bioactivity.

The invention and its further developments are elucidated below by a general description and two illustrative embodiments.

GENERAL DESCRIPTION

The materials used to prepare this bioactive surface layer are one or more metal oxides (MeO), for instance of titanium, chromium, niobium, tantalum and the like or alloys of same in amorphous and/or crystalline form as well as one or more calcium compounds (CaX) composed of portions of calcium phosphates (CaP) and/or calcium apatites (CaAp) and/or calcium carbonate ($CaCO_3$) in crystalline form. The expression herein of "calcium phosphates" (CaP) denotes calcium hydroxyl apatite (hydroxyl apatite, HA), $Ca_5(PO_4)_3OH$ and/or β-tri-calcium phosphate (β-TCP), $Ca3(PO_4)_2$ or similar. The expression "calcium apatite" herein denotes carbonate apatite ($CO_3Ap$), $Ca_{10}(PO_4)_6CO_3$ and/or fluoroapatite (Fap), $Ca_{10}(PO_4)_6F_2$ and/or chloroapatite (ClAp), $Ca_{10}(PO_4)_6Cl_2$ and/or oxyapatite (Oap), $Ca_{10}(PO_4)_6O$. The described mixture is used to coat a preferably metal substrate which may or may not be oxidized. The concentration ratio of MeO to CaX can be selected to be variable or constant across the entire layer thickness. Preferably a variable MeO/CaX ratio will be selected, with a higher value near the metal substrate. The layer thickness may be between 0.01 $\mu$ and 5 mm.

Furthermore impermeable or porous layers may be made. A thickness between 0.01 $\mu$ and 50 $\mu$ was found optimal for impermeable layers; on the other hand, a thickness between 10 $\mu$ and 3 mm was found optimal for porous ones. Preferably the thickness of impermeable layers shall be between 0.5 and 20 $\mu$ and for porous ones between 100 $\mu$ and 1 mm. Appropriately the magnitude of the CaX grains is between 2 nm and 4 mm.

ILLUSTRATIVE EMBODIMENT 1

A 1 m tetrabutylortho titanate ($C_{16}H_{36}O_4Ti$) solution in ethanol is prepared. Next a titanium sol is prepared by slowly adding the same volume of a mixture of water and nitric acid ($HNO_3$) in ethanol. The concentrations shall be selected in such manner that the ratios $Ti/H_2O$ and $Ti/HNO_3$ are resp. 1/2 and 100/1.

Moreover a 0.5 m calcium-nitrate tetrahydrate $[Ca(NO_3).4H_2O]$ solution in ethanol is prepared. Thereupon phosphorus pentoxide ($P_2O_5$) is dissolved in ethanol to form an 1 m phosphoric ester solution

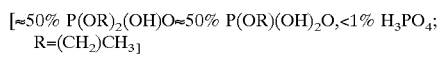

This solution is mixed with the calcium nitrate solution whereby the Ca/P ratio is 10/6. This solution is slowly added to the titanium sol previously prepared.

Various ratios of Ti/Ca may be selected and illustratively the titanium concentration is higher in the layer zone adjacent to the substrate and the calcium-phosphorus compound concentration is higher at the surface of the layer.

Thereupon these mixtures are deposited using dip-coating on the titanium substrate. This operation is repeated several times with solutions of decreasing Ti/Ca ratios. In the process the implant temperature is raised to 350° C. for 5 minutes between each coating. After the last deposition, the coated implant temperature is raised to 850° C. for 5 minutes.

ILLUSTRATIVE EMBODIMENT 2

Citric acid ($C_6H_8O_7$) is dissolved in water in a 4 m concentration. Then tetrabutylortho titanate ($C_{16}H_{36}O_4T$) and acetylacetone ($C_5H_8O_2$) are added. The ratio of ($C_{16}H_{36}O_4Ti$)/$C_5H_8O_2$)/($C_6H_8O_7$) shall be 1/4/4. Moreover a 1 m calcium solution (Ca) of calcium acetate ($C_4H_6CaO_4$) in water is prepared. Next phosphorus pentoxide ($P_2O_5$) is dissolved in ethanol to prepare an 1 m phosphoric acid ester solution

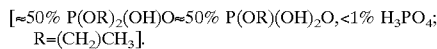
[≈50% $P(OR)_2(OH)O$≈50% $P(OR)(OH)_2O$,<1% $H_3PO_4$; R=$(CH_2)CH_3$].

Thereupon this solution is mixed with the previously prepared solution of tetrabutylortho titanate, acetylacetone and citric acid. Then the previously prepared solution of calcium acetate is slowly added with the Ca/P ratio being required to be 10/6.

Various Ti/Ca ratios may be selected in this manner and accordingly layers can be made of which the zones adjoining the substrate have higher titanium concentrations while on the other hand higher concentrations of the calcium phosphorus compound are higher at the surface.

In the following, the citric acid solution is polymerized by adding ethylene glycol and evaporating the solvent. Thereupon these mixtures must be deposited by dip-coating on the titanium substrate. This procedure is repeated using solutions of decreasing Ti/Ca ratios and the implant temperature is raised to 350° C. for 5 minutes between each coating step. Upon termination of the last coating step, the coated implant's temperature is raised to 850° C. for 10 minutes.

What is claimed is:

1. A bioactive surface layer of a thickness between 0.01 $\mu$ and 5 mm for a metal bone implant, the surface layer being disposed on a substrate and containing calcium compounds (CaX) selected from the group consisting of: calcium phosphate (CaP), calcium apatites (CaAp), and calcium carbonate ($CaCO_3$), the sum of these three substances present in particulate form as (CaX) being defined by the equation:

$$100\% \ (CaX) = \Sigma[x \ \% \ (CaP) + y \ \% \ (CaAp) + z \ \% \ (CaCO_3)]$$

wherein $x+y+z=100$ and $0 \leq x \leq 100$; $0 \leq y \leq 100$; $0 \leq z \leq 100$; and the dimensions of the CaX particles being between 2 nm and 4 mm, wherein the surface layer additionally contains amorphous or crystalline metal oxide (MeO) except for aluminum oxide and wherein molar ratio CaX/MeO in the surface layer selectively increases from a bottom adjacent the substrate toward a top remote from said substrate.

2. Surface layer as claimed in claim 1, characterized in that the molar ratio of CaX/MeO in the surface layer increases preferably continuously from bottom to top toward the free surface.

3. Surface layer as claimed in claim 1, wherein the calcium phosphate is selected from the group consisting of:
  calcium hydroxyl apatite (HA), $Ca_5(PO_4)_3OH$ and
  β-tricalcium phosphate (β-TCP), $Ca_3(PO_4)_2$, and wherein
  $\Sigma[x_1\% \ (HA) + x_2\% \ (\beta\text{-TCP})] = x \ \%$, and $0 \leq x_1, x_2 \leq x$.

4. Surface layer as claimed in claim 1, wherein the calcium apatites is selected from the group consisting of:
  carbonate apatite ($CO_3Ap$), $Ca_{10}(PO_4)_6CO_3$ and
  fluoroapatite (FAp), $Ca_{10}(PO_4)_6F_2$ and
  chloroapatite (ClAp), $Ca_{10}(PO_4)_6Cl_2$ and
  oxyapatite (OAp), $Ca_{10}(PO_4)_6O$,
and wherein
  $\Sigma[y_1\% \ (CO_3Ap) + y_2\% \ (Fap) + y_3\% \ (ClAp)] = y \ \%$, and $0 \leq y_1, y_2, y_3, y_4 \leq y$.

5. Surface layer as claimed in claim 1, wherein an atomic ratio Ca/P of (CaP) in the surface layers is between 1/10 and 10/1.

6. Surface layer as claimed in claim 5, wherein the atomic ration Ca/P of (CaP) in the surface layers is between 1/4 and 4/1.

7. Surface layer as claimed in claim 1, wherein an atomic ratio $Ca/CO_3$ of ($CaCO_3$) in the surface layer is between 1/10 and 10/1.

8. Surface layer as claimed in claim 7, wherein an atomic ratio $Ca/CO_3$ of ($CaCO_3$) in the surface layer is between 1/4 and 4/1.

9. Surface layers as claimed in claim 1, wherein an atomic ratio Ca/P of ($CO_3Ap$) in the surface layer is between 1/10 and 10/1.

10. Surface layers as claimed in claim 9, wherein an atomic ratio Ca/P of ($CO_3Ap$) in the surface layer is between 1/4 and 4/1.

11. Surface layer as claimed in claim 1, wherein an atomic ratio $CO_3/P$ of the ($CO_3Ap$) in the surface layer is between 0/1 and 10/1.

12. Surface layer as claimed in claim 11, wherein an atomic ratio $CO_3/P$ of the ($CO_3Ap$) in the surface layer is between 1/1000 and 2/1.

13. Surface layer as claimed in claim 1, wherein a molar ratio $CaP/CO_3$ Ap in the surface layer is between 1/0 and 0/1.

14. Surface layer as claimed in claim 1, wherein the molar ratio $CaP/CO_3$ Ap in the surface layer is between 1/0 and 2/1.

15. Surface layer as claimed in claim 1, wherein a molar ratio $CaP/CaCO_3$ in the surface layer is between 1/0 and 0/1.

16. Surface layer as claimed in claim 15, wherein the molar ratio $CaP/CaCO_3$ in the surface layer is between 1/0 and 2/1.

17. Surface layer as claimed in claim 1, wherein a molar ratio of $CO_3Ap/CaCO_3$ in the surface layer is between 1/0 and 0/1.

18. Surface layer as claimed in claim 17, wherein the molar ratio of $CO_3Ap/CaCO_3$ in the surface layer is between 10/1 and 1/10.

19. Surface layer as claimed in claim 1, wherein the bioactive surface layer is substantially free of pores.

20. Surface layer as claimed in claim 1, wherein the bioactive surface layer comprises pores of a diameter no more than 1 $\mu$.

21. Surface layer as claimed in claim 19, wherein a thickness of the bioactive, pore-free surface layer is between 0.1 and 50 $\mu$.

22. Surface layer as claimed in claim 19, wherein the thickness of the bioactive, pore-free surface layer is between 0.5 and 20 $\mu$.

23. Surface layer as claimed in claim 1, wherein the thickness of the bioactive surface layer is from 10 $\mu$ to 3 mm, and wherein the surface layer is porous.

24. Surface layer as claimed in claim 23, wherein the thickness of the bioactive surface layer is from 100 $\mu$ to 1 mm.

25. Surface layer as claimed in claim 1, wherein the metal substrate comprises an oxidized surface.

26. Surface layer as claimed in claim 1, wherein the following relation governs the (CaP) portion X:
  $0 \leq x \leq 100$.

27. Surface layer as claimed in claim 26, wherein the following relation governs the (CaP) portion x:
  $50 \leq x \leq 100$.

28. A method for preparing as bioactive surface layer on a metal implant as claimed in claim 1, wherein the metal implant is consecutively dipped into various solutions containing calcium and metal ions and of a decreasing metal/calcium ratio.

* * * * *

UNITED STATES PATENT AND TRADEMARK OFFICE
CERTIFICATE OF CORRECTION

PATENT NO. : 6,221,111 B1
DATED : April 24, 2001
INVENTOR(S) : Piveteau et al.

It is certified that error appears in the above-identified patent and that said Letters Patent is hereby corrected as shown below:

Column 3, claim 4,
Line 60, delete "(Fap)" and insert -- (FAp) --.

Column 4, claim 14,
Line 21, delete "claim 1" and insert -- claim 13 --.

Signed and Sealed this

Thirteenth Day of November, 2001

*Attest:*

*Nicholas P. Godici*

*Attesting Officer*

NICHOLAS P. GODICI
*Acting Director of the United States Patent and Trademark Office*